(12) United States Patent
Cully et al.

(10) Patent No.: US 8,721,704 B2
(45) Date of Patent: May 13, 2014

(54) EXPANDABLE STENT WITH WRINKLE-FREE ELASTOMERIC COVER

(75) Inventors: Edward H. Cully, Flagstaff, AZ (US); Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 618 days.

(21) Appl. No.: 11/408,473

(22) Filed: Apr. 21, 2006

(65) Prior Publication Data

US 2007/0250146 A1   Oct. 25, 2007

(51) Int. Cl.
*A61F 2/06* (2013.01)

(52) U.S. Cl.
USPC .......................................................... 623/1.13

(58) Field of Classification Search
USPC ......... 623/1.2, 1.13, 1.23, 1.39, 1.46, 1.16, 1, 623/1.12, 1.44, 1.11–1.15, 1.17, 1.3, 1.54, 623/23.71
See application file for complete search history.

(56) References Cited

U.S. PATENT DOCUMENTS

| | | | |
|---|---|---|---|
| 4,739,762 A | 4/1988 | Palmaz | |
| 5,534,287 A | 7/1996 | Lukic | |
| 5,653,747 A * | 8/1997 | Dereume | 623/1.54 |
| 5,735,892 A | 4/1998 | Myers et al. | |
| 5,800,522 A | 9/1998 | Campbell et al. | |
| 5,843,164 A * | 12/1998 | Frantzen et al. | 623/1.16 |
| 5,873,906 A | 2/1999 | Lau et al. | |
| 6,015,431 A | 1/2000 | Thornton et al. | |
| 6,156,064 A | 12/2000 | Chouinard | |
| 6,193,745 B1 | 2/2001 | Fogarty et al. | |
| 6,254,627 B1 | 7/2001 | Freidberg | |
| 6,336,937 B1 | 1/2002 | Vonesh et al. | |
| 6,488,701 B1 | 12/2002 | Nolting et al. | |
| 6,923,827 B2 | 8/2005 | Campbell et al. | |
| 2001/0053929 A1 * | 12/2001 | Vonesh et al. | 623/1.12 |
| 2002/0045931 A1 | 4/2002 | Sogard et al. | |
| 2002/0178570 A1 * | 12/2002 | Sogard et al. | 29/516 |
| 2003/0082324 A1 | 5/2003 | Sogard et al. | |
| 2003/0130721 A1 | 7/2003 | Martin et al. | |
| 2004/0024448 A1 | 2/2004 | Chang et al. | |
| 2004/0088042 A1 | 5/2004 | Kim et al. | |
| 2004/0181274 A1 | 9/2004 | Brown et al. | |
| 2004/0265475 A1 | 12/2004 | Hossainy et al. | |
| 2005/0075715 A1 * | 4/2005 | Borges et al. | 623/1.13 |
| 2006/0165754 A1 | 7/2006 | Ranade | |

FOREIGN PATENT DOCUMENTS

| | | |
|---|---|---|
| EP | 1 586 286 | 10/2005 |
| WO | 9712562 | 4/1997 |
| WO | 9938455 | 8/1999 |
| WO | 0033770 | 6/2000 |

* cited by examiner

*Primary Examiner* — Tuan V Nguyen
*Assistant Examiner* — Tin Nguyen
(74) *Attorney, Agent, or Firm* — David J. Johns; Paul J. Fordenbacher

(57) ABSTRACT

An improved stent-graft device is provided that delivers a smooth flow surface over a range of operative expanded diameters by applying a unique cover material to the stent through a technique that allows the cover to become wrinkle-free prior to reaching fully deployed diameter. The unique cover material then allows the device to continue to expand to a fully deployed diameter while maintaining a smooth and coherent flow surface throughout this additional expansion. Employed with a self-expanding device, when the device is unconstrained from a compacted diameter it will self-expand up to a fully deployed diameter with the graft being substantially wrinkle-free over diameters ranging from about 30-50% to 100% of the fully deployed diameter. Preferably, the graft component comprises an elastomeric material, such as silicone, polyurethane, or a copolymer of PAVE-TFE.

5 Claims, 5 Drawing Sheets

EXPANDABLE STENT WITH WRINKLE-FREE ELASTOMERIC COVER

FIELD OF THE INVENTION

The present invention relates to covered stents for use in various medical procedures.

BACKGROUND OF THE INVENTION

The following terms used herein are defined as follows:

The term "stent" means a frame structure containing openings through its wall, typically cylindrical in shape, intended for implantation into the body. A stent may be self-expanding and/or expanded using applied forces.

As used herein, the terms "covered stent" and "stent-graft" are used interchangeably to mean a stent with a cover on at least a portion of its length. The cover may be porous or non-porous and permeable or non-permeable. Active or inactive agents or fillers can be attached to or incorporated into the cover.

Referring to FIG. 4, as used in this application, the term "wrinkle" 65 means a fold in a stent cover 62 that has a larger peak to valley height 64 than a thickness 66 of an adjacent stent strut 68. Wrinkles can extend through the stent opening to beyond either the outer stent-graft surface, inner stent-graft surface, or both. Wrinkles can be observed with unaided vision or they can be observed and measured under magnification, such as optical microscopy. "Wrinkle-free" means a stent covering that is substantially free of wrinkles.

As used herein, the term "self-expanding" means the attribute of a device that describes that it expands outwardly, such as in a general radial direction, upon removal of a constraining means, thereby increasing in diameter without the aid of an external force. That is, self-expanding devices inherently increase in diameter once a constraining mechanism is removed. Constraining means include, but are not limited to, tubes from which the stent or covered stent device is removed, such as by pushing. Alternatively, a constraining tube or sheath may be disrupted to free the device or the constraining means can be unraveled should it be constructed of a fiber or fibers. External forces, as provided by balloon catheters for example, may be used prior to expansion to help initiate an expansion process, during expansion to facilitate expansion, and/or after stent or covered stent deployment to further expand or otherwise help fully deploy and seat the device.

As used in this application, the term "elastomeric" describes the property of a material that can be stretched under relatively low stress and upon immediate release of the stress, will return with force to its approximate original dimensions. The term "elastomer" describes a material that is elastomeric.

As used herein, the term "fully deployed" refers to the state of a self-expanding stent after which the constraining means has been removed and the stent, at about 37° C. over the course of about 30 seconds, has expanded under its own means without any restriction. A portion or portions of a self-expanding stent may be fully deployed and the remainder of the stent may be not fully deployed.

The phrase, "operating diametric range" refers to the diametric size range over which the stent or stent-graft will be used and typically refers to the inner diameter of the device. Devices are frequently implanted in vessel diameters smaller than that corresponding to the device fully deployed state. This operating range may be the labeled size(s) that appear in the product literature or on the product package or it can encompass a wider range, depending on the use of the device.

As used herein, the term "porous" describes a material that contains small or microscopic openings or pores. Without limitation, "porous" is inclusive of materials that possess pores that are observable under microscopic examination. "Non-porous" refers to materials that are substantially free of pores. The term "permeable" describes a material through which fluids (liquid and/or gas) can pass. "Impermeable" describes materials that block the passage of fluids. It should be appreciated that a material may be non-porous yet still be permeable to certain substances.

Stents and covered stents have a long history in the treatment of trauma-related injuries and disease, especially in the treatment of vascular disease. Stents can provide a dimensionally stable conduit for blood flow. Further, stents can prevent vessel recoil subsequent to balloon dilatation thereby maintaining maximal blood flow. Covered stents can provide the additional benefits of preventing blood leakage through the wall of the device and inhibiting, if not preventing, tissue growth through the stent into the lumen of the device. Such growth through the interstices of the stent may obviate the intended benefits of the stenting procedure.

In the treatment of carotid arteries and the neurovasculature, coverings trap plaque particles and other potential emboli against the vessel wall thereby preventing them from entering the blood stream and possibly causing a stroke. Coverings on stents are also highly desirable for the treatment of aneurismal vascular disease. The covers are also useful substrates for adding fillers or other bioactive agents (such as anticoagulant drugs, antibiotics, growth inhibiting agents, and the like) to enhance device performance.

Balloon-expandable stent-grafts have a long history of use in the treatment of vascular disease. Thin, highly elastic biologically inert coatings such as porous polyurethane and PTFE have been taught, for instance, in U.S. Pat. No. 4,739,762 to Palmaz. The Palmaz patent does not teach or suggest applying the coating at stent diameters smaller than the fully deployed diameter. Furthermore, the Palmaz patent's teachings are limited to balloon-expandable stents.

U.S. Pat. No. 6,156,064 to Chouinard teaches the use of dip coating to apply polymers to self-expanding stents. Stents and stent-grafts have been dipped into polymer-solvent solutions to form a film on the stent followed by spray coating and applying a polymeric film to the tube. Stent-grafts comprising at least three layers (stent, graft, and membrane) have been constructed in this manner.

U.S. Patent Application 2004/0024448 A1 to Chang et al. teaches covered stents with elastomeric materials including PAVE-TFE. Self-expanding stent-grafts made with this material, like those made of other materials in the art, are not wrinkle-free over the operating range of the devices. These coverings of self-expanding stents are typically applied to the stent in the fully-deployed state. Consequently, wrinkles are formed when the stent-graft is crushed to any significant degree.

The stent covers may extend along a portion or portions or along the entire length of the stent. Generally, stent covers should be biocompatible and robust. They can be subjected to cyclic stresses about a non-zero mean pressure. Consequently, it is desirable for them to be fatigue and creep resistant in order to resist the long-term effects of blood pressure. It is also desirable that stent covers be wear-resistant and abrasion-resistant. These attributes are balanced with a desire to provide as thin a cover as possible in order to achieve as small a delivery profile as possible. Covers compromise the flow cross-section of the devices, thereby narrowing the blood flow area of the device, which increases the resistance to flow. While increased flow area is desirable, durability can be critical to the long-term performance of covered stents. Design choice, therefore, may favor the stronger, hence thicker, covering. Thick covers, however, are more resistant to distension than otherwise identical thinner covers.

Some balloon-expandable stent covers are wrinkle-free over the operating range of the stents because the extreme pressures of the balloons can distend the thick, strong covers that are placed onto the stent at a less than a fully deployed stent diameter. Even the thinnest covers in the prior art, such as those made of ePTFE (e.g., those taught in U.S. Pat. Nos. 6,923,827 and 5,800,522 to Campbell et al.), however, may be too unyielding to be distended by the radial forces exerted by even the most robust self-expanding stents.

Non-elastic and non-deformable self-expanding stent covers are, therefore, generally attached in a wrinkle-free state to the stent when the stent is fully deployed. When such covered stents are at any outer diameter smaller than the fully deployed outer diameter, the cover is necessarily wrinkled. These wrinkles, unfortunately, can serve as sites for flow disruption, clot initiation, infection, and other problems. The presence of wrinkles may be especially deleterious at the inlet to covered stents. The gap between the wrinkled leading edge of the cover and the host vessel wall can be a site for thrombus accumulation and proliferation. The adverse consequences of wrinkles are particularly significant in small diameter vessels which are prone to fail due to thrombosis, and even more significant in the small vessels that provide blood to the brain.

The use of thin, strong materials is known for implantable devices (e.g., those taught in U.S. Pat. No. 5,735,892 to Myers et al.). Extremely thin films of expanded PTFE (ePTFE) have been taught to cover both self-expanding and balloon expandable stents. Typically, these films are oriented during the construction of the devices to impart strength in the circumferential direction of the device. Consequently, the expanding forces of the self-expanding stents may be far too low to distend these materials. In fact, such devices are generally designed to withstand high pressures. These coverings, like those of other coverings in the art, are wrinkle-free only when the devices are fully deployed.

Stents have also been covered with a continuous layer of elastic material. As taught in U.S. Pat. No. 5,534,287 to Lukic, a covering may be applied to a stent by radially contracting the stent, then placing it inside a tube with a coating on its inner surface. The stent is allowed to expand, thereby bringing it in contact with the coating on the tube. The surface of contact between the stent and the tube is then vulcanized or similarly bonded. No teaching is provided concerning the diameter of the tube relative to the fully deployed stent diameter. The patent specifically teaches in one embodiment the application of the coating on a stent in the expanded condition. The inventor does not teach how to eliminate or even reduce wrinkles in the stent cover. In fact, the patent teaches how to increase the thickness of the coating, a process that would only increase the occurrence of wrinkling.

U.S. Patent Application 2004/0024448 A1 to Chang et al teaches covered stents with elastomeric materials including PAVE-TFE. Self-expanding stent-grafts made with this material, like those made of other materials in the art, are not wrinkle-free over the operating range of the devices. These coverings of self-expanding stents are typically applied to the stent in the fully-deployed state. Consequently, wrinkles are formed when the stent-graft is crushed to any significant degree.

SUMMARY OF THE INVENTION

The present invention is an improved expandable implantable stent-graft device that provides a smooth flow surface over a range of operative expanded diameters. This is accomplished by applying a unique cover material to the stent through a unique technique that allows the cover to become wrinkle-free prior to reaching fully deployed diameter. The unique cover material then allows the device to continue to expand to the fully deployed diameter while maintaining a smooth and coherent flow surface throughout this additional expansion.

In one embodiment the present invention comprises a diametrically self-expanding stent-graft device having a graft covering attached to at least a portion of the stent. The device is adapted to be constrained into a compacted diameter for insertion into a body conduit, which will produce wrinkles along its graft surface. However, when the device is unconstrained from the compacted diameter it will self-expand up to the fully deployed diameter with the graft being substantially wrinkle-free over diameters ranging from 50% to 100% of the fully deployed diameter.

Further improvements in the present invention may include providing an elastomeric graft component, in the form of either a coherent continuous tube or a film tube. Suitable elastomeric materials may include silicone, polyurethanes and various forms of PAVE-TFE copolymers.

By modifying the materials and/or the construction techniques, the range of wrinkle-free expansions can be increased to about 30%-100% or even wider ranges.

DETAILED DESCRIPTION OF THE INVENTION

The present invention addresses the problem of wrinkles in the covers in stent-grafts. The covers of self-expanding stent-grafts heretofore exhibited wrinkles when deployed to diameters smaller than the diameter at which the cover was applied to the stent, which is typically the fully deployed diameter. Inasmuch as body conduits are rarely the exact diameter of the stent-graft, rarely uniformly circular in cross-section, and rarely non-tapered, sections or entire lengths of self-expanding stent-grafts frequently are not fully deployed and hence present wrinkled surfaces to flowing blood or other body fluids. Furthermore, covered stents are often intentionally implanted at less than their fully deployed diameters in order to utilize their inherent radial expansion force to better anchor the devices against the host tissue, thereby preventing device migration in response to blood flow. Such practices come at the expense of having to tolerate devices with at least partially wrinkled covers. The present invention involves the use of a unique stent cover material, one that combines two seemingly mutually exclusive properties—being both strong enough to withstand the forces exerted by constant, cyclic blood pressure and also distensible enough to expand in response to the expansion forces exerted by a self-expanding stent.

In addition, a unique manufacturing method had to be devised in order to utilize this material to construct a self-expanding stent-graft. The temperature-constrained shape-memory properties of self-expanding stents introduce significant processing challenges. Ultimately, a process was developed which entailed applying the cover to the stent in a refrigerated environment.

Figure 1A:
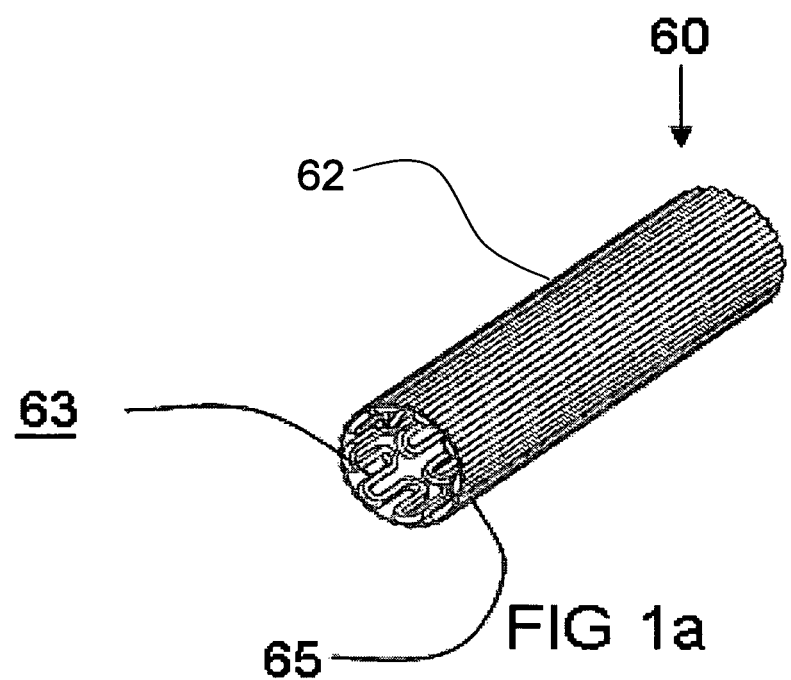
FIG. 1a is a three-quarter isometric view of one embodiment of a covered stent of the present invention in the constrained state having a cover mounted on the outside of the stent.
Figure 1B:
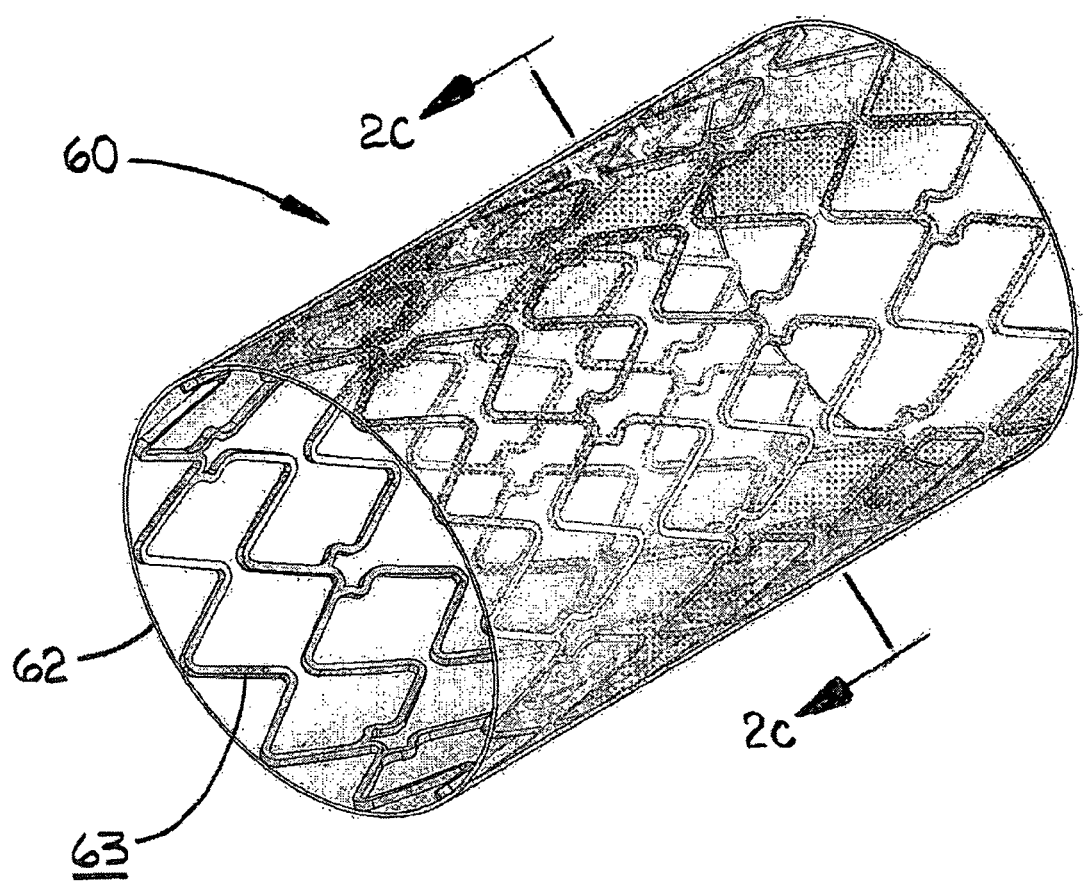
FIG. 1b is a three-quarter isometric view of the embodiment of a covered stent of the present invention of FIG. 1a in the fully deployed state.

Referring to FIGS. 1a and 1b, the present invention is directed to implantable device 60 having a self-expanding stent component 63 with a cover 62 (or both), that is wrinkle-free over an operating diametric range of the device. The cover 62 has wrinkles 65 in the constrained state as shown in FIG. 1a. The wrinkles disappear once the device self-expands to a pre-determined diameter at which the cover was formed on the stent. The cover 62 remains wrinkle-free as the device 60 self-expands even further as shown in FIG. 1b, up to and including the fully deployed diameter. The invention addresses the clinical problems associated with wrinkles in self-expanding stent covers while providing the minimum amount of covering material. Wrinkles are known to disrupt blood flow and can become sites for clot deposition which may ultimately lead to graft thrombosis and embolus shedding. These sequelae may create serious clinical consequences, especially in organs such as the brain. The incorporation of a single, very thin cover enables a stent-graft device with a profile dictated primarily by the stent strut dimensions, not by the mass or volume of the cover. The present invention, therefore, provides a heretofore unavailable combination of deployment diameter for a given size stent-graft and a wrinkle-free cover surface over a wide range of deployed diameters.

For use in the present invention, nitinol (nickel-titanium shape memory alloy) and stainless steel are preferred stent materials. Nitinol is preferred for its shape memory properties. The memory characteristics can be tailored for the requirements of the stenting application during the fabrication of the alloy. Furthermore, nitinol used to make the stent can be in the form of wire that can be braided or welded, for example, or it can be tubing stock from which a stent is cut. While nitinol offers a wide variety of stent design options, it should be appreciated that stainless steel and other materials may also be formed into many different shapes and constructs.

Stent covers of the present invention are preferably durable and biocompatible. The stent covering of the present invention has a low tensile elastic modulus, which enables it to be distended with the minimal force that is exerted by a self-expanding stent. Furthermore, the covering is provided with a minimal (or non-existent) elastic recoil force so that after stent expansion the covering does not cause the stent-graft to decrease in diameter over time. The cover is also preferably thin. Thinness has the multiple benefits of reducing the introduction size of the device, maximizing the blood flow cross-section, providing less resistance to radial expansion, and introducing less elastic recoil.

Preferred cover materials include, but are not limited to, thin elastomeric biomaterials. More specifically, the elastomeric materials include such candidates as polyurethanes, silicone materials, perfluoroethylvinylether-tetrafluoroethylene (PEVE-TFE), perfluoropropylvinylether-tetrafluoroethylene (PPVE-TFE), and the like. Terpolymers containing at least two of the following monomers are also preferred: PEVE, PPVE, perfluoromethylvinylether (PMVE), and TFE. Most preferably, perfluoromethylvinylether-tetrafluoroethylene (PMVE-TFE) is used. These materials are can be applied in various manners such as adhering tubes of the materials to the inner and/or outer surfaces of the stent.

These elastomeric materials are preferably applied by dip coating self-expanding stents into liquid solutions of the covering materials. In order to minimize the stent-graft profile, the stent is coated in such a way that the minimal amount of covering results. Preferably, the cover material that spans the stent openings is thinner than the stent element thickness. In some cases, it may be preferred to have stent cover that is thicker than thickness of the stent element. Such a cover can be created by applying more elastomer by means such as, but not limited to, multiple dip coatings or utilizing a more viscous coating solution. Therapeutic agents, fillers, or the like can be added to the stent cover. The elastomer can also be rendered porous by such means as those known in the art. Porosity in the cover material can, among other benefits, facilitate the attachment of other materials to the cover.

In a preferred embodiment, a nitinol stent is chilled and crushed to a diameter less than the fully deployed outer diameter. The chilling is desirable to help maintain the stent in the crushed state. The covering is then applied without creating wrinkles. The constrained diameter is selected according to the intended operating parameters of the device, such as about 90% of the fully deployed outer diameter or less, about 80% of the fully deployed outer diameter or less, about 70% of the fully deployed outer diameter or less, about 60% of the fully deployed outer diameter or less, and for most applications most preferably about 50% of the fully deployed outer diameter or less. While maintaining the device in the chilled state, the stent-graft is allowed to dry and then further crimped with a chilled crimping tool and transferred into a delivery catheter.

In an alternative preferred embodiment, a nitinol stent is first coated at its fully deployed diameter by dipping it into a liquid solution of the covering material and allowing the cover to dry. The cover is inspected to ensure that it is wrinkle-free. The covered stent is next chilled, and crushed. Crushing a covered stent made in this manner introduces wrinkles into the cover material. Again the crushed diameter may be formed at any desired pre-determined constraint, including about 90% of the fully deployed outer diameter or less, about 80% of the fully deployed outer diameter or less, about 70% of the fully deployed outer diameter or less, about 60% of the fully deployed outer diameter or less, or about 50% of the fully deployed outer diameter or less.

Next, the crushed cover stent is dipped into a chilled solvent solution that will enable the elastomer cover material to re-flow. The re-flowing of the cover material eliminates the wrinkles created during crushing. While maintaining the device in the chilled state, the stent-graft is allowed to dry and then further crimped with a chilled crimping tool and transferred into a delivery catheter.

Stent-grafts made in either of these inventive manners exhibit wrinkle-free coverings over the device diameter range extending from the reduced diameter at which the covering was applied or remodeled (collectively referred to as "formed") up to and including the fully deployed diameter.

Figure 2A:
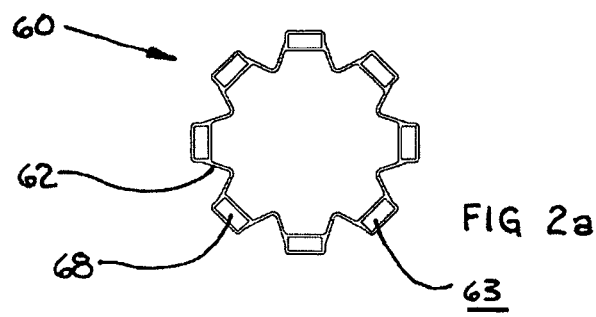
FIG. 2a is a transverse cross-section view of the embodiment of a covered stent of the present invention deployed to 30% of the fully deployed outer diameter of the device.
Figure 2B:
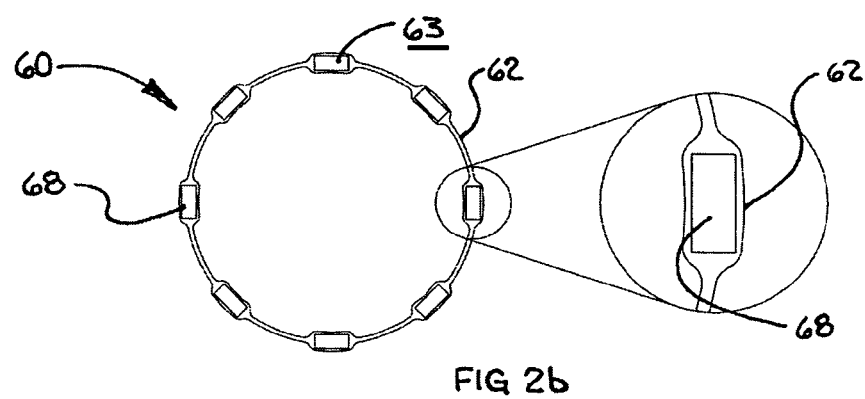
FIG. 2b is a transverse cross-section view of the embodiment of a covered stent of the present invention deployed to 50% of the fully deployed outer diameter of the device with the smooth gradual transition of the adhesive-stent cover interface shown in detail in an enlarged sectional view.

FIG. 2a depicts a cross-section of the covered stent of the present invention that was constructed wrinkle-free at 50% of the fully deployed outer diameter, crimped and transferred inside a delivery catheter, and then deployed to 30% of the fully deployed outer diameter of the device. FIG. 2b illustrates the wrinkle-free stent cover 62 at the diameter at which it was initially bonded to the stent struts 68 of the stent 63, thereby forming the covered stent 60. FIG. 2b also represents the wrinkle-free properties of the cover of a stent-graft in which the cover is applied at the stent fully deployed diameter, then the cover is remodeled at a smaller diameter.

Inner or outer elastomeric covers or both can be attached to the stent 63 at this reduced diameter. They can be attached by any conventional means including, but not limited to, using an adhesive, solvent bonding, or heat bonding. When both inner and outer covers are attached to the stent, they can be applied so as to encase the stent struts 68 as depicted in FIG. 2b.

Figure 2C:
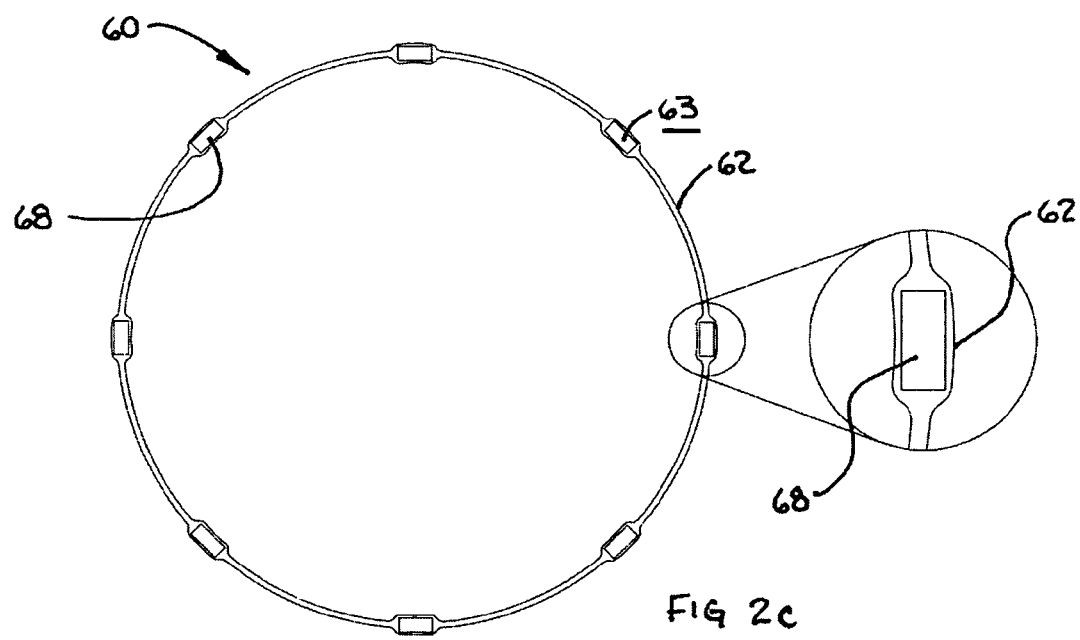
FIG. 2c is a transverse cross-section view of the embodiment of a covered stent of the present invention taken along line 2c-2c of FIG. 1b, deployed to 100% of the fully deployed outer diameter of the device with the smooth gradual transition of the adhesive-stent cover interface shown in detail in an enlarged sectional view.
Figure 3:
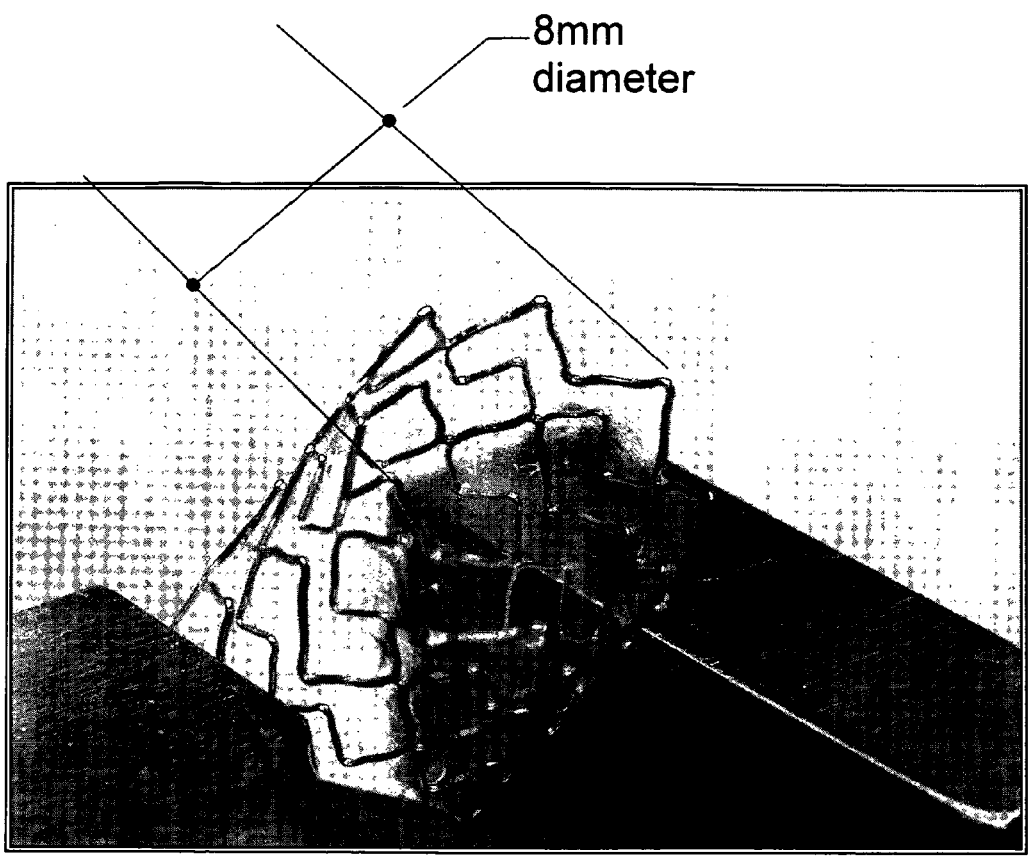
FIG. 3 is a photomicrograph showing covered stent of the present invention that is fully deployed.
Figure 4:
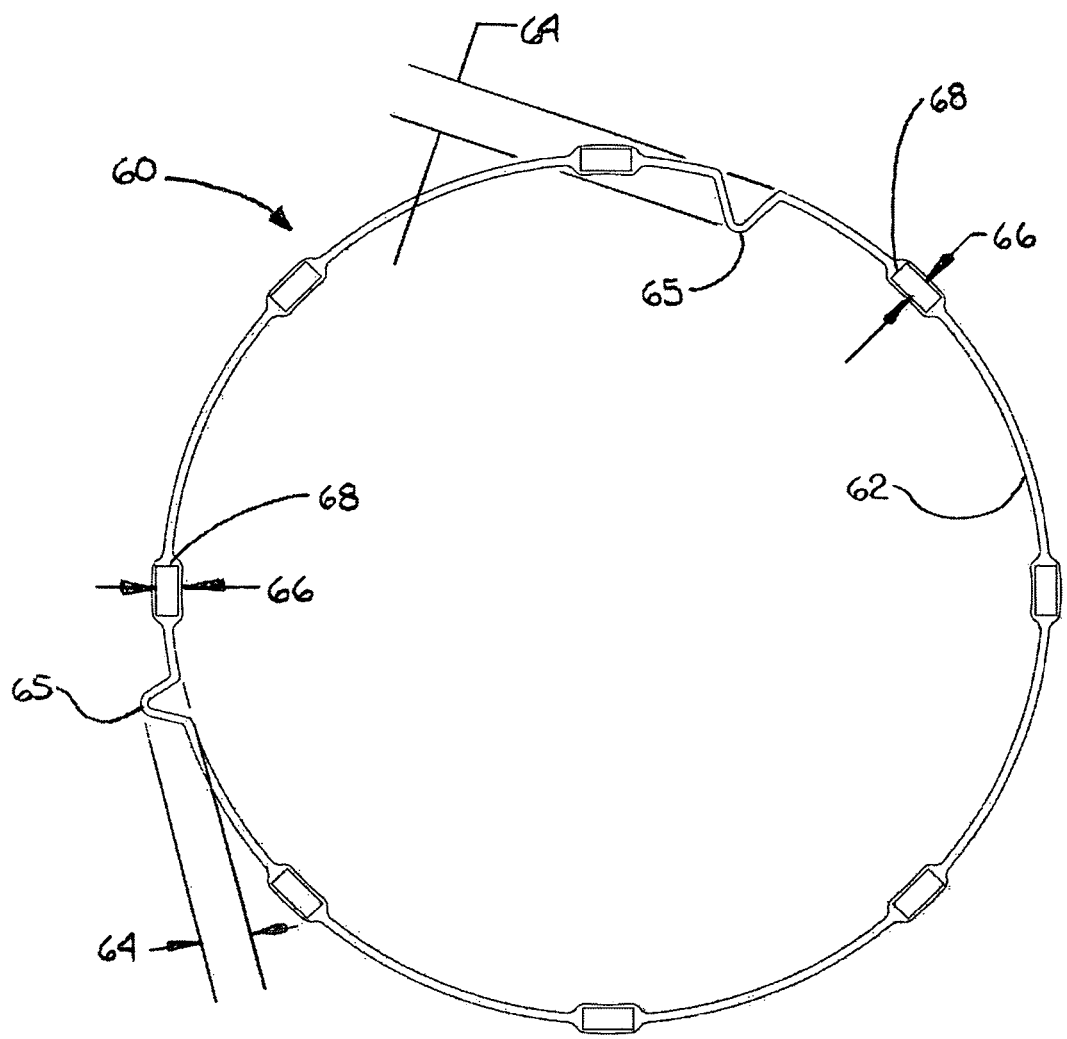
FIG. 4 is a transverse cross-section view of exemplary wrinkles in a cover on the outer surface of the stent.

The thin elastomer cover 62 stretches and remains wrinkle free up to and including the fully deployed diameter as shown in FIG. 2c. In order to achieve this characteristic, the covering must be substantially wrinkle-free at a stent diameter smaller than the fully deployed diameter. This diameter should be no larger than the smallest intended diameter of the implanted device. Crushing the device below the diameter at which the cover was formed induces wrinkles in the stent cover 62 as indicated in FIG. 4 in which the covered stent of FIG. 2b was crushed to enable the device to be transferred to inside a delivery catheter. Forming the covering at an intermediate stent size means less crushing is necessary to decrease the stent-graft diameter for insertion into the delivery catheter. Additionally, the likelihood of perforating the cover during the crushing process is reduced when less crushing is needed.

The wrinkle-free feature of articles of the present invention can benefit the performance of tapered stent-grafts. Tapered grafts are widely used in the treatment of aortoiliac disease. The present invention, which can include or not include a tapered stent and/or cover, can be implanted inside a tapered vessel without exhibiting wrinkles in the cover. That is, regardless of the shape of the starting materials, the device of the present invention can conform to become a tapered self-expanding stent-graft when deployed within a tapered body conduit. This allows tapered body conduits to be treated with non-tapered devices that are easier and less expensive to construct, without deploying an improperly sized stent-grafts. This also allows for a wider range of effective deployable sizes and shapes without the need to increase the number of different configurations of products.

The present invention has particular value in very demanding, small caliber stenting applications. These are applications in which a cover is needed to either protect against plaque or other debris from entering the blood stream after balloon angioplasty or to seal an aneurysm. Perhaps the most demanding applications are those involving the treatment of carotid and neural vessels where even small wrinkles in the stent cover may create a nidus for thrombosis. Given the sensitivity of the brain, the consequences of such thrombus accumulation and possible embolization can be dire. Not only does the present invention overcome the challenging problem of providing a wrinkle-free cover in a viable stent-graft, it accomplishes this with a surprisingly minimal amount of covering material. It was unanticipated that such a distensible, thin, and low mass material could satisfactorily perform as a stent covering.

The following examples are intended to illustrate how the present invention may be made and used, but not to limit it to such examples. The full scope of the present invention is defined in the appended claims.

EXAMPLES

To evaluate the examples, the following test methods were employed.

Testing Methods

Assessment of Wrinkles

Stent-graft device covers were visually examined without the aid of magnification at ambient temperatures. The ends of devices were secured within a hollow DELRIN® resin block in order fix the longitudinal axis of the device at an angle of about 45° above horizontal which enabled viewing the inner surface of the stent-grafts. The devices were positioned to allow examination of free edge of the device and stent openings nearest the ends of the device. Stent-grafts that were not fully deployed were restrained inside rigid tubes during examination. Fully deployed devices were submerged in an about 37° C. water bath prior to examination.

Alternatively, optical or scanning electron microscopy could be used to look for the presence or absence of wrinkles.

Dimensional Measurements

Stent and covered stent outer diameters were measured with the aid of a tapered mandrel. The end of a device was slipped over the mandrel until the end fit snuggly onto the mandrel. The outer diameter of the device was then measured with a set of calipers. Optionally, a profile projector could be used to measure the outer diameter of the device while so placed on the mandrel.

The fully deployed outer diameter was measured after allowing the self-expanding device to fully deploy in a 37° C. water bath, then measuring the device diameter in the water bath in the manner previously described.

For devices restrained inside restraining means having a round cross-section, the device outer diameter in the restrained state was taken to be the inner diameter of the restraining means.

In order to examine a device at some percentage of the fully deployed diameter of the device, the fully deployed diameter must first be known. A length of a device can be severed from the entire device and its fully deployed diameter can be measured. For example, a length of the device can be released from the delivery catheter and its diameter measured after being fully deployed in a 37° C. water bath.

Inventive Example 1

A tubular, self-expanding nitinol stent constructed using the pattern as described in FIG. 4 of U.S. Pat. No. 6,709,453 was obtained. The stent had an outer diameter of approximately 8 mm and a length of about 30 mm. The stent was processed in the following manner. A liquid solution of PMVE-TFE, a liquefied thermoplastic fluoropolymer as described in Example 5 of US Patent Application 2004/0024,448 of Chang, et al. was also obtained. PMVE-TFE is an elastomeric material. A relatively dilute solution, 3% by weight, of the polymer was utilized. The stent was dipped into the elastomer solution. The dipped, now covered, stent was removed from the solution, examined to ensure that the elastomer bridged all of the stent openings, and allowed to dry for four hours.

The elastomer covered stent-graft, a polymer diluting solution FC-77 (3M Fluroinert, 3M Specialty chemicals Division, St Paul, Minn.), tweezers, and a crimping device (such at taught in US 2002/0138966 A1 to Motsenbocker) were chilled together in a conventional freezer compartment set to −15° C. The chilled crimping device was used to uniformly reduce the diameter of the stent along its length to about 4 mm. Using chilled tweezers, the following procedure was performed inside the freezer compartment. This step introduced wrinkles in the elastomeric stent cover.

The stent was dipped into the chilled FC-77 solution for approximately 3 seconds. This allowed the elastomer to slightly re-flow, which eliminated the wrinkles in the stent cover. Performing these process steps at cold temperatures (in the freezer) enabled handling of the compacted, unrestrained nitinol stent without warming it enough to induce the device to self-expand. The dipped and re-flowed covered stent was removed from the solution and examined while still inside the freezer to confirm that the elastomer bridged all of the stent openings and that the cover was wrinkle-free. The wrinkle-free device was allowed to dry for four hours inside the freezer.

Next, the crimping device was again used, to crush the elastomer-covered stent to a delivery diameter of approximately 2 mm. The resultant stent-graft had a delivery profile of about 2 mm. Next, the device was transferred from its 2 mm delivery profile constraining sheath into a hollowed DELRIN® resin block with an inner diameter corresponding to about 50% of the fully deployed outer diameter of the device, which corresponds to the size at which the device was made. Microscopic examination verified the absence of wrinkles in the cover at this diameter.

The device was then released from the constraining block and allowed to fully self-expand in a 37° C. water bath. The device expanded to the starting outer diameter of 8 mm. The cover exhibited no wrinkles during expansion or at this fully-deployed state.

Comparative Example 2

The advantage of making the stent-graft of the present invention in the above-described manner is apparent upon comparing the device of Example 1 with a device made in accordance with the teachings of the prior art. Another covered stent was made in the exact manner as described above but without including the inventive step of the crushing the stent and re-flowing the elastomer at a diameter in between the fully deployed and delivery diameters. That is, the comparative covered stent was never chilled and crushed to 50% of the outer diameter, nor dipped in a solvent solution in order to allow the elastomeric covering to re-flow. Instead, under ambient conditions, the 8 mm covered stent was crushed to 50% of the outer diameter and then transferred into the hollowed constraining block. The comparative (prior art) device, unlike the inventive device, exhibited wrinkles at 50% of the fully deployed outer diameter.

Inventive Example 3

A tubular, self-expanding stent-graft was made in accordance with the teachings of Example 1 except for the following differences. In this case, a different inventive step was applied to create the wrinkle-free cover. Silicone material (MED-1137 Silicone Adhesive, NuSil Silicone Technology, Carpinteria, Calif.) was used to create the elastomeric covering. A liquid elastomer solution of silicone and heptane was also obtained. A relatively dilute solution, 1% by weight, of the elastomer was created. The stent, elastomer solution, tweezers, and a crimping device were chilled together inside a conventional freezer compartment set to −15° C.

The chilled crimping device was used to uniformly reduce the diameter of the stent along its entire length. The outer diameter of the stent was reduced to about 4 mm. The following procedure was performed inside the freezer compartment using the chilled tweezers. The stent was dipped into the chilled elastomer solution. The dipped, now covered, stent was removed from the solution, examined to ensure that the elastomer bridged all of the stent openings, and allowed to dry for four hours inside the freezer.

Next, the crimping device was used again to further crush the elastomer-covered stents to a delivery diameter of approximately 2 mm. The resultant stent-graft had a delivery profile of about 2 mm. The device was transferred from its 2 mm delivery profile constraining sheath into a hollowed DELRIN® resin block with an inner diameter corresponding to about 50% of the fully deployed outer diameter of the device. This 50% of the fully deployed outer diameter corresponded to the outer diameter at which the device was made. Microscopic examination verified the absence of wrinkles in the cover at this diameter.

The device was then released from the constraining block and allowed to fully self-expand in a 37° C. water bath. The device expanded to the starting outer diameter of 8 mm. The cover exhibited no wrinkles at this fully-deployed state.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A method for producing a self expanding stent-graft device that comprises
   providing a stent having a fully compacted diameter, a fully expanded diameter, and an intermediate diameter between the fully compacted diameter and the fully expanded diameter;
   orienting the stent at its fully expanded diameter;
   forming an elastomeric cover on the stent to form the stent-graft;
   orienting the stent at its intermediate diameter at a temperature less than the temperature that would induce the stent to self-expand; and
   re-flowing the elastomeric cover at a temperature less than the temperature that would induce the stent to self-expand to be substantially wrinkle-free at such intermediate diameter,
   wherein the stent-graft is substantially wrinkle-free when self expanding from the intermediate diameter to the fully expanded diameter of the stent.

2. The method of claim 1 that further comprises compacting the resulting stent-graft and placing into a delivery system before said stent warms to a temperature that would induce the stent to self-expand.

3. The method of claim 1, wherein said elastomeric cover is dipcoated onto the stent.

4. The method of claim 1, wherein said elastromeric cover comprises at least one of the materials selected from the group consisting of polyurethanes, silicone materials, perfluoroethylvinylether (PEVE), tetrafluoroethylene (TFE), perfluoropropylvinylether (PPVE), perfluoromethylvinylether (PMVE), perfluoroethylvinylether-tetrafluoroethylene (PEVE-TFE), perfluoropropylvinylether-tetrafluoroethylene (PPVE-TFE), and perfluoromethylvinylether-tetrafluoroethylene (PMVE-TFE).

5. The method of claim 4, wherein said material is perfluoromethylvinylether-tetrafluoroethylene (PMVE-TFE).

* * * * *